US00PP37155P2

(12) United States Plant Patent
Lim

(10) Patent No.: US PP37,155 P2
(45) Date of Patent: Dec. 16, 2025

(54) ***HIBISCUS* PLANT NAMED 'ALTbirdy'**

(50) Latin Name: *Hibiscus rosa-sinensis*
Varietal Denomination: ALTbirdy

(71) Applicant: Altman Specialty Plants llc, Vista, CA (US)

(72) Inventor: Peter Lim, Escondido, CA (US)

(73) Assignee: Altman Specialty Plants LLC, Vista, CA (US)

( * ) Notice: Subject to any disclaimer, the term of this patent is extended or adjusted under 35 U.S.C. 154(b) by 0 days.

(21) Appl. No.: 19/022,269

(22) Filed: Jan. 15, 2025

(51) Int. Cl.
*A01H 6/60* (2018.01)
*A01H 5/02* (2018.01)

(52) U.S. Cl.
USPC ..... Plt./257

(58) Field of Classification Search
USPC ..... Plt./226, 257
See application file for complete search history.

(56) References Cited

U.S. PATENT DOCUMENTS

PP31,721 P2 * 5/2020 Whitcomb ..... A01H 5/02
Plt./257

* cited by examiner

*Primary Examiner* — Karen M Redden

(57) ABSTRACT

A new and distinct cultivar of *Hibiscus* plant named 'ALTbirdy' is disclosed, characterized by creamy yellow flowers with large red center feathering out to the majority of the flower. Flowers have thick petals. Plants are dwarf and compact, around 2 feet tall and 2 feet wide. Foliage is uniquely elliptic-shaped. The new variety is a *Hibiscus*, typically produced as an ornamental plant.

1 Drawing Sheet

Latin name of the genus and species: *Hibiscus rosa-sinensis*.

Variety denomination: 'ALTbirdy'.

BACKGROUND OF THE INVENTION

The new *Hibiscus* cultivar is a product of a planned breeding program conducted by the inventor, Peter Lim. The objective of the breeding program was to produce vigorous *Hibiscus rosa-sinensis* cultivars with healthy foliage. The cross resulting in this new variety was made Aug. 16, 2014.

The seed parent is the unpatented *Hibiscus rosa-sinensis* 'Lilikoi Yellow' unpatented. The pollen parent is the unpatented variety *Hibiscus rosa-sinensis* 'Moody Blue' unpatented. The new variety was identified and selected as a potentially interesting selection in September of 2016. Selection was made at a commercial nursery in Vista, California.

Asexual reproduction of the new cultivar 'ALTbirdy' was first performed in September 2016 in Vista, California, by vegetative cuttings. Subsequent propagation has shown that the unique features of this cultivar are stable and reproduced true to type in successive generations.

SUMMARY OF THE INVENTION

The cultivar 'ALTbirdy' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTbirdy'. These characteristics in combination distinguish 'ALTbirdy' as a new and distinct *Hibiscus* cultivar:

1. Creamy yellow flowers with large red center feathering out to the majority of the flower.
2. Blooms occur in clusters
3. Dwarf, compact plant with a size of about 2 feet by 2 feet.
4. Unique elliptic-shaped foliage.
5. Thick petals.

PARENT COMPARISONS

Plants of the new cultivar 'ALTbirdy' are similar to the seed parent 'Lilikoi Yellow', in most horticultural characteristics. However, characteristics of the new cultivar differ in the following:

1. Plants of the new cultivar are much smaller than plants of the seed parent.
2. Flower color of the new cultivar is a different shade of yellow than the seed parent, which is a brighter, darker yellow.
3. The new cultivar has a much larger red center than the seed parent.

Plants of the new cultivar 'ALTbirdy' are similar to the pollen parent, in most horticultural characteristics. However, characteristics of the new cultivar differ in the following:

1. Plants of the new cultivar are much smaller than plants of the pollen parent.
2. Flower color of the new cultivar is creamy yellow with a large red center; flower color of the pollen parent is lavender blue with creamy yellow margins.

COMMERCIAL COMPARISON

Plants of 'ALTbirdy' are similar in some horticultural characteristics to the variety *Hibiscus* 'Minoakaakala', unpatented. The new variety, however, differs in the following:

1. Center flower color of 'ALTbirdy' is red; center flower color of 'Minoakaakala' is red fading into light purple with a gold halo.
2. Plants of 'Minoakaakala' are much larger than plants of 'ALTbirdy'.
3. Flowers of 'ALTbirdy' are smaller than flowers of 'Minoakaakala'.
4. Foliage of 'ALTbirdy' are smaller than foliage of 'Minoakaakala'.

Plants of 'ALTbirdy' are similar in some horticultural characteristics to the variety *Hibiscus* 'Hope', unpatented. The new variety, however, differs in the following:

1. Flowers of 'ALTbirdy' are smaller than flowers of 'Hope'.
2. Plants of 'Hope' are taller than plants of 'ALTbirdy' by about 50%.
3. Flowers of 'ALTbirdy' have a red center; center color of 'Hope' is dark red fading to pink with a yellow halo.
4. Foliage of 'ALTbirdy' are smaller than foliage of 'Hope'.

BRIEF DESCRIPTION OF THE PHOTOGRAPH

The accompanying photograph illustrates in full color a typical flower of 'ALTbirdy' from a plant grown outdoors at a commercial nursery in Vista, California. The photograph was taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart 2015, except where general terms of ordinary dictionary significance are used. The following observations and measurements describe an 'ALTbirdy' plant. This plant was grown at a commercial nursery in Vista, California. The growing temperature ranged from about 7° C. to 30° C. during the day and from about 5° C. to 12° C. during the night. No artificial light, photoperiodic treatments were given to the plants. Measurements and numerical values represent averages of typical plant types.

Botanical classification: *Hibiscus rosa-sinensis* 'ALTbirdy'.

PROPAGATION

Typical method: Hardwood stem cuttings.

Root Description: Roots are fine, fibrous and well branched. Tan/brown in color, not effectively measured with a color chart.

PLANT

Plant type: Tender, woody flowering shrub.
Age of Plant Described: 6 months old in a 1-gallon pot.
Growth Habit: Compact.
Height: 25 cm.
Plant Spread: 25 cm.
Branching Characteristics: 2 to 4 breaks from a pinch, occurring at an average 45° angle.
Length of Primary Lateral Branches: 10 to 22 cm.
Quantity of Lateral Branches: Each primary lateral branch has 2 to 4 laterals.
Characteristics of Primary Lateral Branches:
- *Diameter*.—Average range 8 to 9 mm.
- *Color*.—New growth RHS Green 143B. Mature growth RHS Green 138B, striated Greyed-Green 197A.
- *Texture*.—New growth very sparsely hirsute, older growth striated.

Internode length: Average range 2 to 3 cm.

FOLIAGE

Leaf:
- *Arrangement*.—Alternate.
- *Quantity*.—Average 6 to 12 per branch.
- *Leaf internode*.—8 to 15 mm.
- *Average Length*.—7 to 10 cm, excluding petiole.
- *Average Width*.—7 cm.
- *Shape of blade*.—Broad elliptic.
- *Apex*.—Acute.
- *Base*.—Obtuse.
- *Margin*.—Entire or irregularly and shallowly crenate.
- *Aspect*.—Moderately undulating and upwardly folded.
- *Texture of top surface*.—Glabrous.
- *Texture of bottom surface*.—Sparse and very short hirsute.
- *Color*.—Young foliage upper side: RHS Green 139A. Young foliage under side: RHS Green 137C. Mature foliage upper side: RHS Green 139A. Mature foliage under side: RHS Green 137C.
- *Venation*.—Type: Pinnate. Venation color, upper side: RHS Green 138B. Venation color, under side: RHS Green 138B.
- *Petiole*.—Length: 2.2 cm. Diameter: 3 mm. Color: Near RHS Green 143B. Texture: Densely short hirsute.
- *Leaf Stipule*.—Not observed.

FLOWER

Natural flowering season: Late Spring through Summer.
Flower type and habit: Solitary, rotate.
- *Single, double, multiplex*.—Single.
- *Petals overlapping*.—Strongly overlapping.

Quantity of flowers: A plant of about 1-year old has approximately 10 open flowers at one time during Summer.
Rate of flower opening: About 3 days from bud to fully opened flower.
Flower Longevity on Plant: 2 days.
Persistent or Self-Cleaning: Self-cleaning.
Bud:
- *Shape*.—Ovate.
- *Length*.—5 cm.
- *Diameter*.—2 cm.
- *Color*.—RHS Orange-Red 34D, light streaks Yellow 12C.

Flower size:
- *Diameter*.—9 cm.
- *Depth*.—7 cm to end of protruding stamen.

Petals:
- *Quantity*.—5.
- *Arrangement*.—Whorled, strongly overlapping.
- *Length*.—5.8 cm.
- *Width*.—5 cm.
- *Shape*.—Slightly asymmetrical broad spatulate.
- *Apex*.—Obtuse rounded with irregular, shallow crenations.

*Base*.—Attenuate.
*Margin*.—Entire. Moderate undulation.
*Texture*.—Glabrous all surfaces. Moderately rugose top and bottom.
*Color*.—When opening, upper surface: RHS Yellow 12A. Large basal blotch (covering most of petal surface) Red 46A at eye, changing to Red 46C and finally feathering out to 45C at outermost eye. Margin Yellow 9B. When opening, lower surface: RHS Yellow-Orange 16C, basal area Red-Purple 58C and 58D. Veins 58A. Lightly flushed 47C over petal blade. Fully opened, upper surface: RHS Yellow-Orange 14C. Large basal blotch (covering most of petal surface) Red 46A at eye, changing to Red 46C and finally feathering out to 45C at outermost eye. Margin Yellow 8A. Fully opened, lower surface: RHS Yellow-Orange 16C, basal area Red-Purple 58C and 58D. Veins 58A. Lightly flushed 47C over petal blade. Ratio of basal blotch/eye to petal size: Overall about 70% of petal blade is blotched. 40% solidly blotched, 30% feathered blotch. Feathering: Strong feathering from center of petal surface.

Sepals:
*Quantity*.—5.
*Length*.—1.8 cm.
*Width*.—1.2 cm.
*Shape*.—Deltate.
*Margin*.—Entire.
*Apex*.—Acute.
*Base*.—Fused.
*Color*.—Upper surface: RHS Green 143C veins 143A. Lower surface: RHS Green 143D veins 143A.
*Texture*.—Upper surface: Softly pubescent. Lower surface: Very short hirsute.

Epicalyx:
*Quantity of Bracts*.—6.
*Bract Length*.—1.5 cm to 1.9 cm.
*Bract Width*.—3 to 4 mm.
*Bract Shape*.—Straplike.
*Bract Margin*.—Entire.
*Color*.—Upper surface: RHS Green 137C. Lower surface: Near RHS Green 137D.
*Texture*.—Upper surface glabrous, lower surface non-pubescent rough.

Peduncle:
*Length*.—3 cm.
*Diameter*.—4 mm.
*Angle*.—Approximately 45° to the lateral branch.
*Strength*.—Strong.
*Texture*.—Sparsely hirsute.
*Color*.—RHS Green 143A.

Fragrance: No fragrance.

REPRODUCTIVE ORGANS

Stamens:
*Number*.—About 40.
*Filament Length*.—7 mm.
*Filament color*.—Near Orange 27D.

Anthers:
*Shape*.—Irregular sphere.
*Length*.—About 3 mm.
*Color*.—Near RHS Yellow-Orange 17B.
*Pollen color*.—Near RHS Yellow-Orange 17B.
*Pollen amount*.—Moderate.

Pistil:
*Number*.—1.
*Length*.—6 cm.
*Style*.—Length: 5 cm. Color: Lower section near Red 53C, Upper 1/3 Red 43D.
*Stigma*.—Shape: Peltate. Color: Near RHS Red 40A.
*Ovary color*.—Near RHS Yellow-Green 150D.
*Ovary length*.—1 cm.
*Ovary width*.—6 mm.

OTHER CHARACTERISTICS

Seeds: Not observed.

Disease/pest resistance: Neither resistance nor susceptibility to normal diseases and pests of *Hibiscus rosa-sinensis* have been observed.

Temperature tolerance: USDA Zones 8 through 11.

What is claimed is:

1. A new and distinct cultivar of *Hibiscus* plant named 'ALTbirdy' as herein illustrated and described.

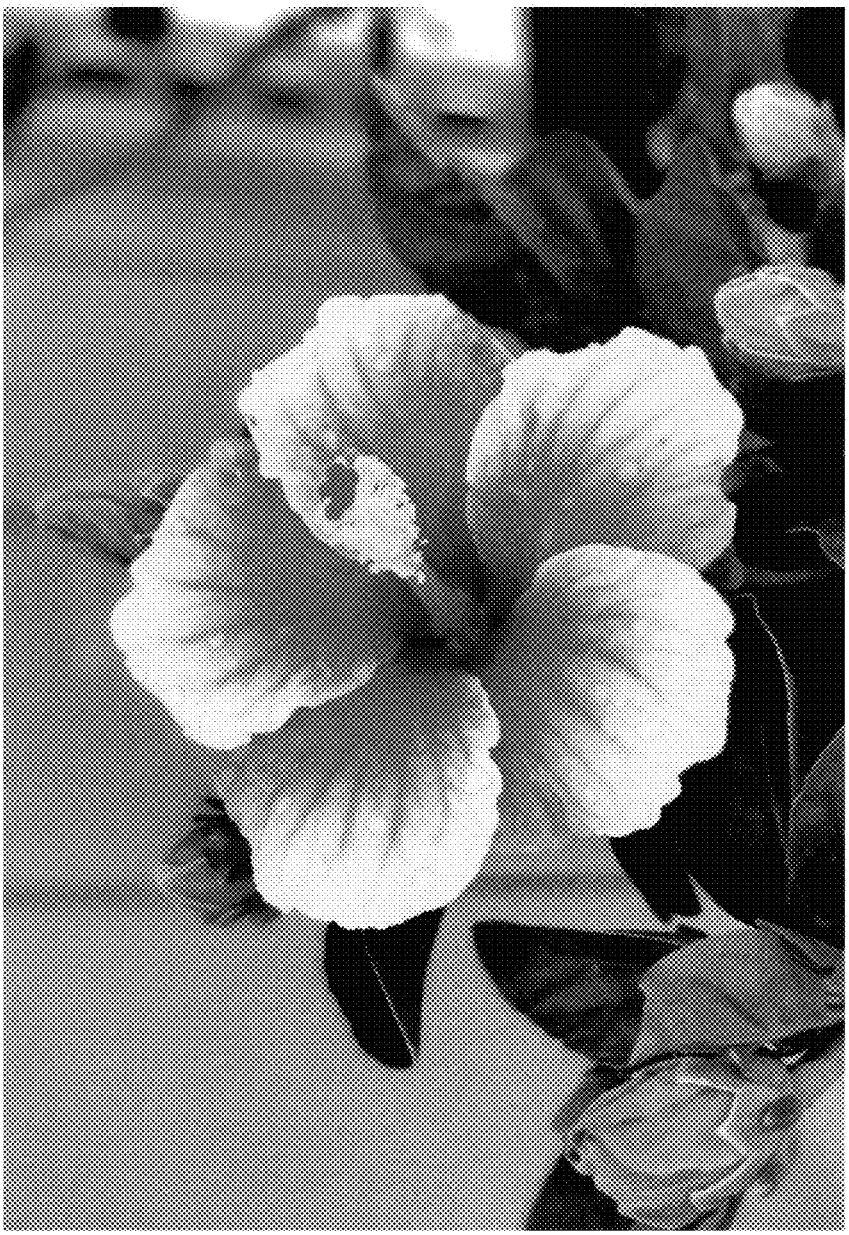

* * * * *